(12) United States Patent
Brodard et al.

(10) Patent No.: US 7,381,192 B2
(45) Date of Patent: Jun. 3, 2008

(54) THERAPEUTIC AND/OR TRAINING DEVICE FOR A PERSON'S LOWER LIMBS USING A MECHANICAL ORTHETIC DEVICE AND A NEUROMUSCULAR STIMULATION DEVICE

(75) Inventors: Roland Brodard, Villeneuve (CH); Reymond Clavel, Oulens/Echallens (CH)

(73) Assignee: Fondation Suisse pour les Cybertheses, Villeneuve (CH)

( * ) Notice: Subject to any disclaimer, the term of this patent is extended or adjusted under 35 U.S.C. 154(b) by 602 days.

(21) Appl. No.: 10/476,671

(22) PCT Filed: May 10, 2002

(86) PCT No.: PCT/CH02/00255

§ 371 (c)(1),
(2), (4) Date: Nov. 4, 2003

(87) PCT Pub. No.: WO02/092164

PCT Pub. Date: Nov. 21, 2002

(65) Prior Publication Data
US 2004/0172097 A1 Sep. 2, 2004

(30) Foreign Application Priority Data
May 16, 2001 (CH) .................................. 0910/01

(51) Int. Cl.
*A61H 1/02* (2006.01)
*A61N 1/00* (2006.01)
*A61N 1/18* (2006.01)

(52) U.S. Cl. .............................. 601/5; 601/33; 601/34; 607/48

(58) Field of Classification Search .................. 601/5, 601/23, 32, 31, 33, 34, 35; 607/47, 48
See application file for complete search history.

(56) References Cited

U.S. PATENT DOCUMENTS 4,586,495 A * 5/1986 Petrofsky ........................ 602/2

(Continued)

OTHER PUBLICATIONS

Popovic, E. et al. "Hyhybrid assistive System Motor Neuroprosthesis"—IEEE Transaction on Biomedical Engineering, IEEE Inc., New York, US. vol. 36, No. 7, Jul. 1, 1989, pp. 729-737.*
Popovic, D. et al., Hybrid Assistive System—The Motor Neuroprosthesis, IEEE Transactions on Biomedical Engineering, IEEE Inc., New York, US, vol. 36, No. 7, Jul. 1, 1989, pp. 729-736.

*Primary Examiner*—Danton DeMille
(74) *Attorney, Agent, or Firm*—Clifford W. Browning; Krieg DeVault LLP

(57) ABSTRACT

The invention concerns a therapeutic device comprising a mechanical orthotic element (2, 3, 4) designed to constitute a contact surface with at least the patient's lower limbs and a neuromuscular stimulation element (33) including at least a pair of electrodes (37, 38) designed to act on the muscle or muscular group concerned of said patient's limb. The orthotic element comprises two orthoses including each three segments (2, 3, 4) designed to co-operate (11, 13; 12, 14; 15) with respectively the patient's thigh, leg and foot. The first segment is connected at one of its ends through a first motorised articulation (9) to an element (10) designed to co-operate with the patient's body at his hips and at its other end through a second motorised articulation (7) to one of the ends of the second segment. The other end of the second segment is linked through a third motorised articulation (8) to the third segment. Each of the articulations (6, 7, 8) is provided with an angular sensor and force and torque sensors, coupled to the control member (31) of the stimulation device so as to enable feedback control by closed loop adjustment of the stimulation device.

22 Claims, 4 Drawing Sheets

U.S. PATENT DOCUMENTS

| | | |
|---|---|---|
| 4,653,479 A | 3/1987 | Maurer |
| 4,798,197 A * | 1/1989 | Nippoldt et al. ............... 601/34 |
| 4,825,852 A * | 5/1989 | Genovese et al. ............ 601/34 |
| 5,228,432 A * | 7/1993 | Kaiser et al. ................. 601/34 |
| 5,239,987 A * | 8/1993 | Kaiser et al. ................. 601/34 |
| 5,255,188 A | 10/1993 | Telepko |
| 5,368,546 A * | 11/1994 | Stark et al. ................... 601/34 |
| 5,399,147 A * | 3/1995 | Kaiser ......................... 601/34 |
| 5,682,327 A * | 10/1997 | Telepko ....................... 601/34 |
| 5,954,621 A | 9/1999 | Hruska, Jr. et al. |

* cited by examiner

FIG. 1
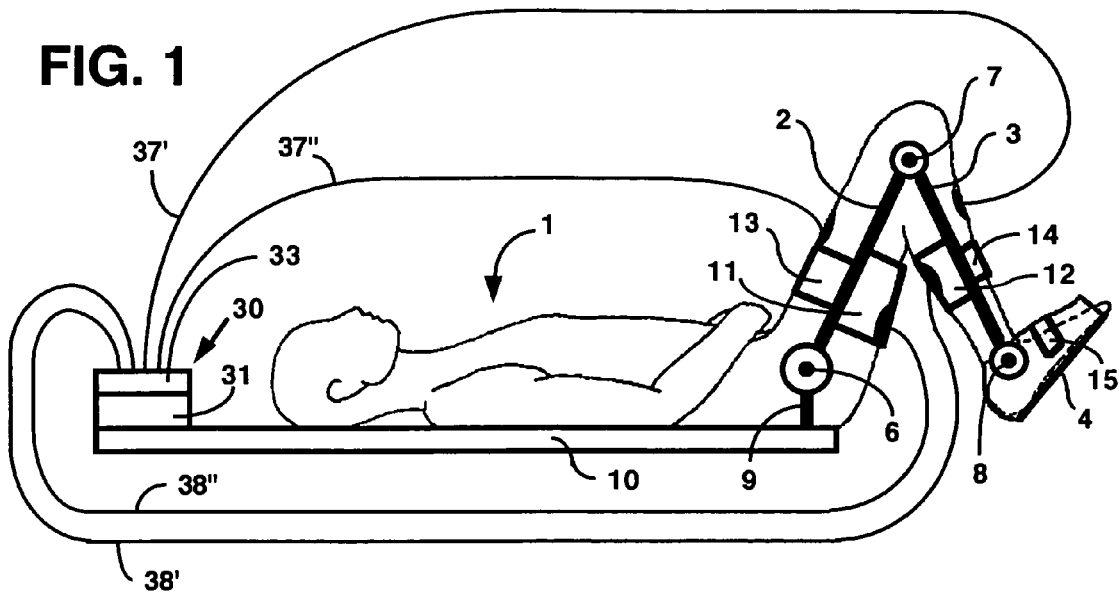
FIG. 2a  FIG. 2b
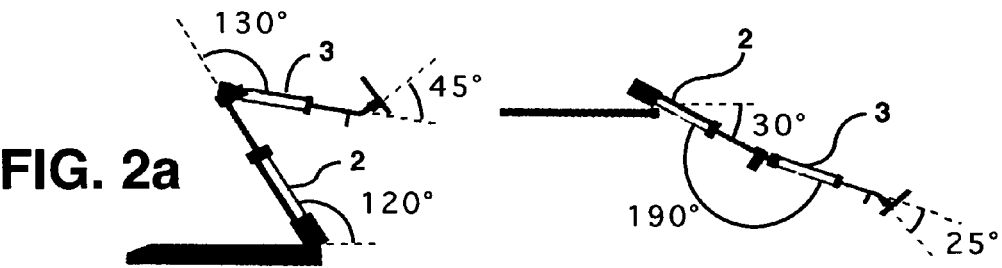
FIG. 3a
FIG. 3b
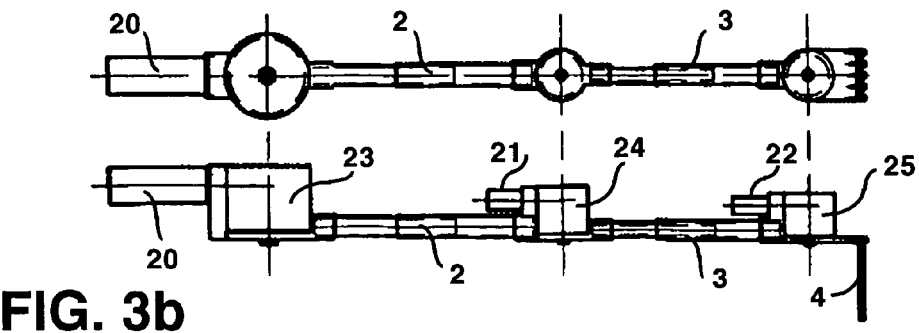

THERAPEUTIC AND/OR TRAINING DEVICE FOR A PERSON'S LOWER LIMBS USING A MECHANICAL ORTHETIC DEVICE AND A NEUROMUSCULAR STIMULATION DEVICE

The present invention concerns a device for re-educating and/or training the lower limbs of a person, in particular a person having an impairment of the central nervous system (paraplegia, hemiplegia).

In the current state of the way in which medullary paralysed persons are dealt with medically, it can be found that, out of 100 new cases, only 20% of persons have suffered total impairment of the spinal cord and are thereby condemned to definitive paralysis, but that 80% show only partial impairment of the spinal cord.

Having regard to the current possibilities of re-education, it is established that approximately 10% to 15% of these 80% of persons who are only partially impaired can regain autonomous walking of relatively satisfactory quality.

This recovery is explained by the fact that the central nervous system (CNS) and, in particular, the spinal cord demonstrate a great capability of "plasticity", that is to say, following a reorganisation of the sublesional nerve circuits of the spinal cord, nerve circuits which are not afflicted, which are still healthy, may be substituted for destroyed nerve circuits in order to fulfil their functions.

This capacity for substitution by plasticity of the nervous system requires veritable reteaching of the motor scheme, which can be initiated and stimulated by the constant repetition of the normal movements which the limbs executed before paralysis. However, with a view to achieving maximum efficacy of re-education, in performing these movements, the closest possible mimicry of the initial intentional movements should be complied with, with active participation of the muscles concerned, and scrupulously complying with the resistance loads which opposed these movements.

This is because, essentially, this reorganisation of substitution by plasticity of the nervous system and reteaching of the motor schema will be determined by the nerve information supplied to the CNS by the proprioceptive nervous system and, more precisely still, by the closed control loop made between the proprioceptive nervous system and the motor nerves (motor neurones) of the muscles concerned.

One essential point must be clearly stated here: the contraction of any muscle responsible for a movement is under the control of the proprioceptive nervous system on which the said muscle depends. This nervous system comprises proprioceptors, which are receptors, at the origin of a sensitive nerve fibre, sensitive to the stimulations produced by the movements of the body. These receptors are situated close to the bones, joints and muscles. The proprioceptive nervous system (which represents deep sensitivity) forms, with the muscles which it controls, a subtle and precise closed-loop control system, which allows control of the movements and of the position of the body.

The result of paralysis is a serious functional handicap which may be aggravated by a whole range of complications; bedsores, spasticity, osteoporosis, circulatory, urinary and intestinal disorders and musculo-tendon plus capsulo-ligamentary retractions.

Muscular atrophy is associated with a musculo-tendon retraction. As a result the muscle loses its strength and endurance. Consequently it loses its capacity to provide functional work.

Capsulo-ligamentry retraction is also a major and very frequent complication which may cause a limitation in articular amplitude (ankylosis) and incorrect attitudes. With time, it may also have a repercussion on the articular cartilage.

It is therefore imperative to prevent these various complications, and in particular the musculo-tendon-articular problems, by regularly mobilising the patient from the very start of his lesion by a re-education programme well-established according to the lesion. It is also essential for the patient to be verticalised as quickly as possible so that he is in a physiological position providing regularisation of the various metabolisms and many physiological functions.

The limbs affected by paralysis are normally subjected to a passive mobilisation method, achieved by an external force intervention. This external force may be supplied directly manually by a therapist or by suitable equipment.

To achieve specific training in addition with a view to the restoration of walking, using a reorganisation of substitution by plasticity of the spinal cord—as described above—it is possible to verticalise the patient whilst supporting him by means of a harness on a conveyer belt, whilst he bears on parallel bars through his upper limbs. The therapist, whilst crouching, then manually causes a movement of the legs which is similar to walking.

This is a process which at the present time is still usual, although it has many drawbacks: the movements imposed are slow and imprecise. The therapist is rapidly exhausted by his crouching position and the work supplied. The result is excessively short sessions with a small number of repetitions of the movements, which considerably reduces the efficacy.

A recent improvement to this process has been achieved (the Lokomat equipment from the Swiss company Hocoma AG) by pure robotisation of this process. A motorised functional mechanical orthesis fulfils the role of an exoskeleton and causes an automatic movement of the lower limbs which reproduces the kinematics of walking on a conveyer belt.

The advantage of this method is that it makes it possible to dispense with the manual intervention of a therapist. There is consequently an improvement in speed, precision and repeatability. It is also possible to repeat the movements as desired.

However, all the methods described above have two major drawbacks. Firstly, these are still purely passive limb mobilisation methods. As a result, lacking any active muscular participation, the efficacy of such methods is limited and all clinical experience demonstrates that they do not suffice to check the atrophy and ankylosis of the paralysed parts of the body. Secondly, these methods are purely static, the patient remaining stationary on a conveyer belt. Consequently there is no relearning of the creation and then management of the kinetic energy and of the conservation of the quantity of movement, created by a movement of the patient and which constitute the very basis of the dynamics of walking with two feet in dynamic equilibrium.

In addition, for a few years, functional electrical stimulation has been proposed for replacing physiological control during walking in patients who have certain minor deficits. This electrical stimulation has been developed to stimulate a certain number of muscles allowing a standing position (Jaeger et coll., 1990) or for improving walking (Carnstam et coll., 1977). More recently, a whole series of works have shown the possibility, with complicated and heavy equipment, of restoring the walking of paraplegics by electrical stimulation. However, this re-education requires considerable expenditure of energy and applies only to a certain number of patients with a relatively low medullar lesion. As a result the restoration of truly functional walking has not yet been achieved.

This lack of success may be explained to a great extent by two major drawbacks common to all the methods of electrostimulation known at the present time.

The first drawback is that they use conventional electrostimulation, the only one currently used, known as open-loop control, characterised by the fact that the stimulation is purely and simply imposed on a muscle, with an absence of retrocontrol (feedback) of the activity thus caused.

It must be stated that developing a movement by electrical stimulation remains tricky. Control of the speed and amplitudes proves sensitive and particularly difficult when the action is performed with additional resistance loads, or very rapidly, following high force pulses which confer high acceleration on it, as in the process of walking with two feet.

This control must be even more precise, repeatable and reliable, for mobilising paralysed limbs. This is because, firstly, mobilisation must always be gentle and progressive and, moreover, as there generally exists a deficit in sensation, the person no longer perceives sensations coming from the paralysed limb thus mobilised.

As a result the use of open-loop controlled electrostimulation does not allow adequate control of the movements caused. The movements thus induced are not able to create and manage kinetic energy and the conservation of the quantity of movement, essential to the correct achievement of truly functional walking which is economic in energy. This amounts to saying that this type of stimulation is not able to produce and then manage the dynamics of the process of walking with two feet.

In fact, it must be stated that the movements thus generated prove to be just capable of accomplishing, more or less roughly, the mere kinematics of walking. Which amounts to stating that these movements are in some way followers of the movement of the body, the latter being generated by another method described below.

The second drawback of the electrostimulation method is essentially a consequence of the first: all the methods described at the present time require significant intervention of the upper limbs which bear either on parallel bars or on a walking frame. The movement of the body is consequently essentially caused by a manual forward movement of the walking frame, which causes a forward movement of the centre of gravity of the body and thus places it in a position of falling forwards, controlled by the bearing of the upper limbs on the said walking frame. Then, under the action of the electrostimulation, a following movement of one lower limb and then the other is caused. Next, the walking frame is moved forwards again and so on.

As a result the walking thus obtained consists of a series of accelerations and then decelerations (brakings) with on each occasion a brief intermediate stop for moving the walking frame forwards. The consequence—currently common to all the methods—is an extremely slow walking, best scarcely one fifth of the normal speed of a pedestrian, requiring an enormous expenditure of energy which very rapidly exhausts the patient. The capacity for movement under such conditions does not exceed a few tens of metres.

Finally, this type of orthetic walking is characterised in that it is statically stable on four bearing points (the two feet and the two hands by means of the walking frame) and does not preserve the quantity of movement, whilst human walking on two feet is characterised in that it allows control of a dynamically stable walking on two bearing points with conservation of the quantity of movement.

Conventional electrostimulation, open-loop controlled, has an additional drawback when it is used with a view to obtaining muscular strengthening. It was described above that this type of stimulation does not allow effective and adequate control of the dynamic activity generated by the muscle stimulated, especially when the latter must contract against additional resistance loads. Which is necessarily the case during a muscular reinforcement training, because of the "overload principle" or "progressive resistance exercise principle".

This is because it is well known that the development of muscular strength and endurance—or musculation—, that is to say the development of the maximum work capacity, depends on a principle known as the "overload principle". According to this principle, the force and endurance of the muscle develop only if the latter is used by a certain amount of time, at the maximum of its power and endurance against a suitable resistance. The overload principle implies that the resistance to which the muscle is opposed must be progressively increased, as the muscle acquires strength and endurance. It is for this reason that the original term "overload principle" has now become the term "progressive resistance exercise principle".

For obvious reasons of effectiveness, precision and safety, this type of open-loop controlled stimulation should be confined essentially to the obtaining of isometric contractions, also referred to as static, since isometric contraction is characterised by an absence of shortening of the muscle, whose ends remained fixed during a contraction.

If the principles of physics are referred to, the consequence of this absence of shortening and movement of the ends of the muscle is that no mechanical work is provided. Nevertheless, the isometric activity consumes energy which is dissipated in the form of heat.

It is clear from the specialised literature that such isometric contractions develop isometric strength only, and this only at a given articular angle and only at this angle.

However, as a general rule, for the purpose of functional re-education, it is sought to increase the strength and endurance of a muscle over the entire range of physiological articular angle, normally operational, which it is able to generate, that is to say to increase its capacity to provide a maximum amount of mechanical work. It is consequently obvious that open-loop controlled electrostimulation is unable to satisfy these requirements.

Generally, when a person is afflicted by a medullar lesion which causes paralysis, it suffers firstly a spinal shock which requires acute care and an initial phase in bed. Subsequently, when it is possible to undertake a first early re-education mobilisation, which must always be gentle and progressive at this stage, the patient already shows pronounced muscular atrophy, consequent upon this period of immobilisation.

Moreover, the large majority of the population of paraplegics are currently in a phase very much later than the initial phase in bed and because of this have more pronounced muscular atrophy frequently accompanied by articular ankylosis.

Initially, the muscular weakness due to immobilisation atrophy and possible restrictions to the articular mobility of the segments of the limb due to ankylosis do not make it possible to support the weight of the body in the vertical position with a view to its mobilisation. Consequently training of muscular strengthening and articular mobility must be able to be carried out in a position favourable to the total mobility of each of the articulations concerned, that is to say, for the lower limb, the ankle, the knee and the hip. To do this, a position lying on the back (dorsal decubitus) would be optimum.

Consequently it would be necessary on the one hand to train articular mobility in order to reinforce the ligamentary and capsular system, and to very progressively eliminate any angular restrictions and to recover, as far as possible, complete mobility of the articulation over its entire physiological angular extent. Moreover, it would be necessary, in parallel, to carry out suitable musculation, in accordance with the "progressive resistance exercise principle (overload principle)", over the entire articular angular extent available. This musculation must be able to be executed both in articular extension and flexion movements of the various segments of the limb concerned, in order to avoid creating any muscular imbalance. Naturally, the musculation of paralysed muscles can be carried out only by means of suitable electrostimulation.

At the start, these exercises should be carried out in an extremely gentle, precise and progressive manner, particularly with regard to articular mobilisation, in order to prevent any damage to the musculo-tendon-articular system and, in particular, the risk of osteoma (of the POA type) due to forced mobilisation.

Paraosteoarthropathy (POA) consists of an ectopic ossification which develops around the large sublesional articulations during certain disorders of the central nervous system (paraplegia, hemiplegia, cranial traumatism etc). It represents a complication which can be redoubtable and feared if it interferes with the function.

Thus, for all the reasons mentioned above, the movements induced must necessarily be rigorously controlled in terms of force, speed and articular amplitude. As seen above, conventional electrostimulation, open-loop controlled, may not be satisfactory for these requirements.

The essential objective of the training described above is to enable the patient to recover and then to maintain a functional work capacity (in some way a level of "fitness") of the lower limbs which, as far as possible, is capable of maintaining the weight of the body in the vertical position, or better still, be capable of making it pass from a crouching position to the vertical position and vice-versa. At this stage only, the patient will be truly able to undertake, with optimum benefit, a specific training of the process of walking on two feet.

It was described above that, in the context of an effective training for walking, the capacity for substitution by plasticity of the nervous system fulfils an essential role and that this capacity is initiated and stimulated by the proprioceptive information. To this end, and for the reteaching of the essential motor scheme, the proprioceptive information will be all the more effective when it is close to that resulting from an equivalent intentional activity (the principle of mimicry).

Highly schematically, in its essentials, it is necessary to consider that walking on two feet takes place in purely dynamic equilibrium on two support points. It is brief force impulses at the very start of a step, delivered by the extensor muscles of the thigh on the hip and by the extensor muscles of the foot, which provide the forward propulsion of the body. These force impulses, or impetus impulses, cause a forward acceleration of the body mass. Thus this body mass acquires a speed and, consequently, a kinetic energy and a quantity of movement. These impulses create the dynamics of the process of walking.

Then, during the execution of the step, the centre of gravity of the body follows a pseudo-ballistic path parabolic in appearance. During the execution of this path, a relatively weak muscular participation provides control of the kinematic chain of the segments which make up the lower limb. It can be said that, at this stage, the muscular participation provides the following of the path and, consequently, manages the dynamics of the process of walking.

The objective of this management is to optimise the movements of the limbs in order to minimise the reduction in kinetic energy at the end of the step and thus to preserve a quantity of movement which is as constant as possible, so that, at the start of the following step, an impulse of minimum strength is sufficient to compensate for the loss of kinetic energy and provide the conservation of the quantity of movement, thus providing propulsion at a constant average speed. It is precisely this degree of conservation of the kinetic energy at the end of each step which determines the new quantity of energy, which will be necessary for maintaining propulsion at a constant average speed.

The mechanism described above is particularly well shown in running on foot. This consists of an acceleration of the speed of unfolding of the kinematics of the process of walking. In this case, during a step, following a high impetus pulse, the physical centre of gravity follows a parabolic ballistic path, during which the two feet leave all contact with the ground, until the weight of the body is received on a single foot at the end of the step. Then the same foot and leg give a new force impulse which provides the following step.

At the present time there exists no device for re-educating the lower limbs of a paraplegic person, nor of training for walking, which fulfils the conditions set out above, so as to be able to train the lower limbs physiologically, respecting a close mimicry of the intentional activity which has become impossible or restricted, following a paralysis of central origin. Likewise, none of the devices proposed up to now in the literature make it possible to achieve the conditions set out above.

The patent U.S. Pat. No. 4,642,769 describes a system for controlling the movements of the lower limbs, achieved in open muscular chain, by means of electrostimulation of the paralysed muscles. These are external means not incorporated in the articulation and this device appears to be effective only with difficulty.

The patents U.S. Pat. No. 5,476,441 and U.S. Pat. No. 5,954,621 describe devices which provide control of the angle of an articulation by means of a retrocontrolled braking of the articular angle. This is however a single braking without the possibility of motorisation of the said articulation.

The patent U.S. Pat. No. 5,682,327 proposes a device which provides universal control of the motors and consequently of the movements generated by means of well known continuous passive mobilisation appliances. As their name specifies clearly, these appliances cause purely passive articular movements. This device is specifically intended for controlling mobile splints activated by motors. However, it does not provide any associated controlled use of any neuromuscular electrostimulation.

So-called hybrid devices, which combine neuromuscular electrostimulation with an orthesis are described in WO 96/36278 and in the article by Popovic D. et al.: "Hybrid Assistive System—The Motor Neuroprosthesis" (IEEE Transactions on Biomedical Engineering, IEEE Inc. New York, US, Vol. 36, No 7, Jul. 1, 1989, pages 729-736). However, these devices have a major drawback, in that the inherent weight of the orthesis is not controlled. Because of this, this weight interferes through its inertial and gravitational effects, and through the forces due to the functional friction with the desired movements of the electrostimulated physical segments, thus profoundly interfering with the quality of the movements required, especially when the movements must be executed at high speed, against load resistances, or for training in walking.

The aim of the present invention is to propose a device for re-educating the lower limbs and training for walking, according to the precharacterising clause of claim 1, which is free from the drawbacks (defects) enumerated above and which satisfy the conditions set out above, so as to provide physiologically optimum re-education training of the lower limbs, and then training for walking, whilst complying with the closest mimicry of intentional active training.

To this end, the invention concerns a device for re-educating and/or training the lower limbs of the patient having an impairment of the central nervous system (CNS), comprising a mechanical orthetic device arranged to constitute an interface with at least one of the lower limbs of the patient and a neuromuscular stimulation device comprising at least one pair of electrodes intended to act on the relevant muscle or muscle group of the said limb of the patient, the said orthetic device comprising at least one articulation provided with an angular sensor and at least one force sensor, the said sensors being coupled to the device controlling the stimulation device so as to allow retrocontrol by closed-loop control of the said stimulation device, characterised in that the said articulation of the orthetic device is provided with a motor controlled by a closed-loop control system by means of the said angular sensor and force sensor, in a manner which is coordinated with the retrocontrol of the stimulation device.

Achieving effective closed-loop control of the articular movements makes it absolutely necessary to be able to measure precisely the articular angles with suitable position sensors, as well as the forces which act at the articulations by means of suitable torque sensors.

In the prior art there do not exist any suitable implantable sensors. Thus the use of essential sensors requires them to be incorporated in an exoskeleton which constitutes a functional orthesis. This functional orthesis also has the function of supporting and guiding the segments of the limbs during exercises and it is also it which has the function of producing and transmitting to the segments of the limbs the load resistances which are essential to effective musculation.

Consequently the orthesis must be constructed in a sufficiently robust manner to effectively fulfil all the functions required. The robustness of the orthesis and all the elements which make it up (sensors, motors, etc.) impose an appreciable weight on each of its movable elements.

However, and this is an essential requirement, during its functioning and particularly at high speed, the orthesis must under no circumstances interfere through its own weight with the physiological conditions of the movements aimed at and achieved by the subject exercising.

In other words, all the inertial and gravitational effects and the effects of functional friction of the orthesis must be able to be neutralised, so that the physical presence of the orthesis must be forgotten (be totally neutralised) for the movements executed to freely and faithfully mimic the corresponding intentional movements.

These requirements are achieved by virtue of the active control of the articular movements inherent in the orthesis, because of the motorisation of the articulations of the orthesis controlled by the closed-loop control system, achieved with articular position and torque sensors, connected to a control unit, under the control of suitable software.

The retrocontrols of the stimulation device and motors will preferably be achieved by control software of the a priori type so as to provide continuous control in real time, these distinct retrocontrols are managed in a coordinated manner by means of suitable software adaptable by programming to each of the various objectives aimed at.

Preferably also the control software incorporates a mathematical modelling of the characteristics and movements of the orthetic device and a mathematical modelling of the behaviour of the muscles.

The following description, given by way of example, refers to the drawing, in which:

FIG. 1 illustrates schematically a first embodiment of the device according to the invention;

FIGS. 2a and 2b show schematically the two extreme positions of the orthesis of the device in FIG. 1;

FIGS. 3a and 3b are views respectively lateral and from the top of an example embodiment of the orthesis in FIG. 1;

Figure 4:
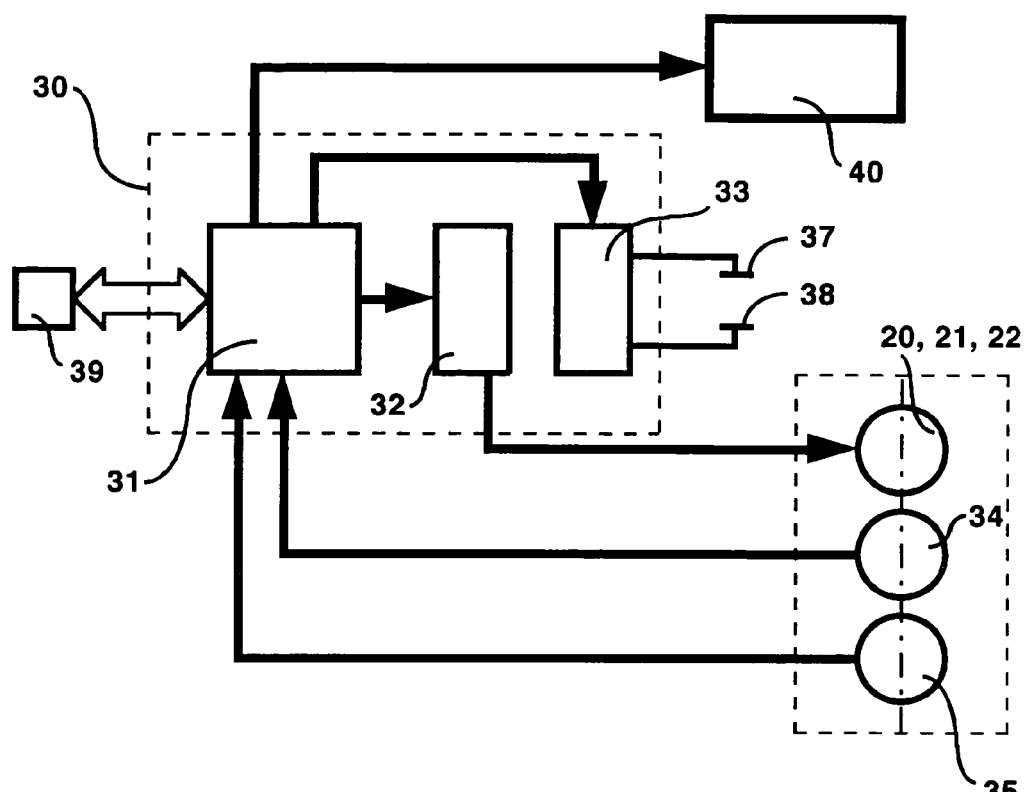
FIG. 4 shows a block diagram of the articular motorisation system of the device in FIG. 1 and its retrocontrol.

An orthesis is said to be "hybrid" when it associates a functional mechanical orthesis with a neuromuscular electrostimulation.

According to the first embodiment of the device depicted in FIG. 1, the device comprises a hybrid orthesis for driving the lower limbs, arranged for use in the position lying on the back (dorsal decubitus).

According to this embodiment, the device allows the exercise of the movement of an injured person in order to re-educate the motor and articular functions as far as possible whilst reducing the risk of bedsores, with a view to restoring functional usage of these limbs.

More precisely, this orthesis consists of two identical ortheses, one for each leg of the patient 1, each of the ortheses being fixed, by means of an articulation 6, and by means of an adjustable support 9, to the end of a horizontal frame 10, duly padded and intended to support the back and pelvis of the patient in the position lying on the back. Each of the two orthesis constitutes a robotic system of the serial type, composed of three segments 2, 3, 4, connected by articulations 7, 8.

Each of the ortheses is arranged so as to produce an exoskeleton for supporting and guiding the lower limb, thus providing a mechanical interface with the three body segments which make up the lower limb, namely the thigh, the leg and the foot.

To this end, the parts of the lower limb (thigh and leg) can be connected to the corresponding segments 2, 3 of the mechanical orthesis by means of padded supports in the form of a channel 11, 12 and straps 13, 14 with "Velcro" type closure connected to the orthetic structure.

As depicted in FIGS. 2a, 2b, 3a and 3b, the orthetic segments 2, 3 of the thigh and leg consist of telescopic tubes whose length can be adapted to the morphology of the patient, so that the orthetic articulations 6 of the hip, 7 of the knee and 8 of the ankle coincide from a functional point of view with the corresponding physiological articulations of the patient. The third orthetic segment 4 constitutes a plantar support. The foot is kept constantly pressed against this plantar support by means of a flexible structure, which is like the upper structure of a shoe, being able to be closed firmly by flexible tongues 15 with a closure of the "Velcro" type.

The interface described, closely connecting the physical segments of the lower limb to the corresponding orthetic segments, thus constitutes a functional unit: the movements of the limb and of the orthesis will consequently be connected and identical.

The kinematics of the serial type of each orthesis, which comprises only one kinematic chain, is the simplest possible. The advantages of such a serial system are fairly numerous, since this system can very easily be adjusted to the morphology of the patient. It can be folded easily and automatically. The three articulations being independent, control is very simple. But above all, as depicted in FIGS. 2*a* and 2*b*, the articular mobility allowed by such a system is maximum and allows optimum training of the articular mobility, over its entire physiological extent. This is because such a training requires, for each of the articulations, the following movement amplitudes, respectively in extension and flexion:

articulation of the hip: $-5°$ to $120°$
articulation of the knee: $-10°$ to $130°$
articulation of the ankle: $-25°$ to $45°$.

However, of course, the orthesis can also be produced with kinematics of the parallel type.

As depicted in FIGS. 3*a* and 3*b*, each articulation of the orthesis is actuated by an electric servomotor 20, 21, 22, able to have a driving effect or a braking effect, coupled to a gearbox 23, 24, 25. Each motor is placed alongside one of the tubes (orthetic segments) connecting the articulations. The axis of the motor is parallel to the adjacent tube. It drives the perpendicular shaft of the articulation by means of a pair of bevel gears. Thus the motor shaft is provided with a bevelled pinion which meshes in a fixed ring on the input shaft of the gearbox, the output shaft of the gearbox being fixed to the other tube connected to the articulation, which it can thus drive.

The motors meeting the requirements of this application can be servomotors of the "Maxon motor" brand. This is because the weight and performance in terms of torque of these motors are excellent. In addition, these motors, benefiting from a modular construction, incorporate a digital position coder.

According to a variant, the articulation is motorised by means of a lever mechanism, actuated by a movement screw. According to this variant, a motor is fixed to one of the two orthesis segments attached to the articulation concerned. This motor causes the rotation of a worm. The rotation of the worm drives a nut mounted on this worm. This nut, by means of a linkage, causes the movement of a crank. The axis of rotation of the crank corresponds to the axis of rotation of the articulation and the crank is fixed to the second orthesis segment attached to the articulation concerned. The result of this device is that, according to the direction of rotation of the motor, the nut moves closer to the motor, which causes an extension of the articulation. A reverse rotation of the motor causes the nut to move away and causes a flexion of the articulation concerned.

According to another variant, the assembly can be arranged so that each motor drives the perpendicular shaft of the articulation by means of a tangent screw with a left-hand helical gear. According to yet another variant, the motors can be placed perpendicular to the adjacent tube.

Naturally the electric servomotors can be replaced by hydraulic servomotors with a suitable hydraulic control device.

Likewise the digital coders can be replaced by analogue coders.

Force and torque sensors are also integrated in each orthetic articulation.

A central control unit 30 is integrated in the device. It comprises, as depicted in the diagram in FIG. 4, a management microcomputer 31, an electrical supply 32 for the servomotors and an electrical neuromuscular stimulator 33.

Figure 5A:
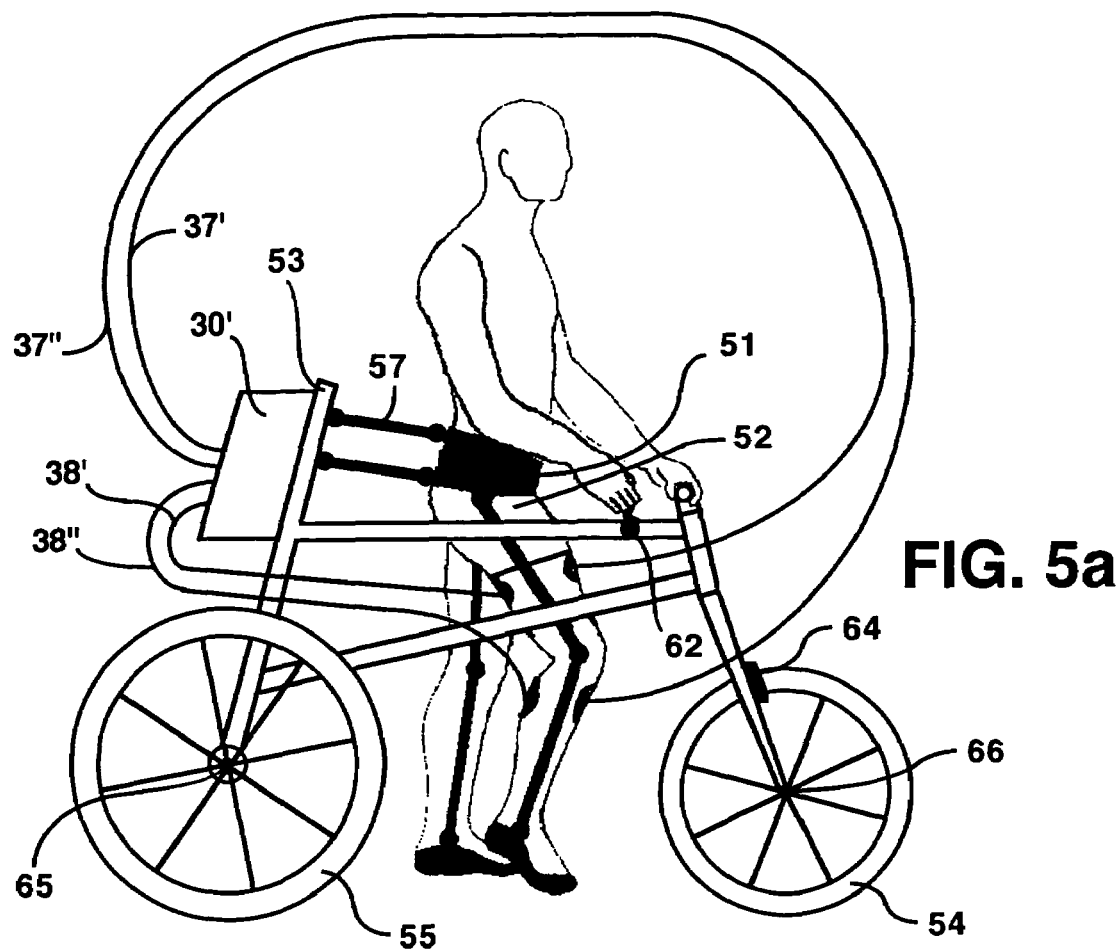
FIGS. 5a and 5b illustrate schematically, respectively in side view and from the top, a second embodiment of the device according to the invention.

The electrical neuromuscular stimulator 33 is programmable with multiple output channels, for example fifteen to twenty channels. This is an electrical-pulse generator, for generating pulses of any shape, for example of rectangular current with a duration of around 200 to 300 µs each. The amplitude of the current of each pulse can be adjusted to between 0 and 100 mA, whilst the repetition frequency of the pulses can be adjusted to between 5 and 80 Hz. The channels are electrically isolated galvanically from each other and from earth (floating outputs), in order to prevent any intracorporeal electrical interaction between the channels in activity. Each channel can be provided with a pair of surface electrodes 37, 38 which can be applied to the muscle to be stimulated. Only two pairs of electrodes 37', 38' and 37", 38" are depicted in FIGS. 1 and 5*a*. However, of course, other pairs of electrodes can be provided. Likewise the surface electrodes can be replaced by a system implanted in the body.

The channels are programmable independently of each other interactively, in order to be able to cause individual contractions, duly controlled for duration and intensity, of each of the muscles stimulated, with a view to a coordinated action of the synergetic and antagonistic muscles in a programmed movement.

The development of the orthetic articulations was dictated by the choice which was made to incorporate the gearboxes directly therein. A relatively compact system was sought which was applicable to the hip, the knee and the ankle. Since the system had to be compact and to have a fairly high reduction factor, gearboxes of the "Harmonic Drive" type can advantageously be chosen. Such a gearbox, with an original design, advantageously replaces a conventional gearbox. It is compact with a low weight.

The design adopted for the orthetic articulations makes it possible to align the segments connecting the articulations as depicted in FIGS. 3*a* and 3*b* so that the entire orthesis remains close to the leg of the patient, for the purpose of improving the quality and precision of the functional unit produced by the orthesis/leg assembly.

The digital position coder 34 and the force and torque sensors 35 integrated in the articulation, mobilised or braked by its servomotor 20, 21 or 22, transmit their information in real time to the central control unit. The management microcomputer 34 of the control unit 30 interprets these data, which makes it possible to know in real time the articular angular position and the angular acceleration and speed of the articulation, as well as the forces and torques which are developed therein.

The management microcomputer 34 contains software in which a mathematical modelling of the orthesis has been recorded, which takes account, for each segment of the orthesis, of its weight, its centre of gravity and the lever arms with respect to the articulations concerned. The torques at the articulations can also be modelled. It is thus possible to model all the free or programmable paths which can be envisaged, such as for example the movements passing from the crouching position to the vertical position, from the sitting position to the vertical position, pedalling, walking, etc. Such a modelling makes it possible to provide for all the movements and their effects, in particular the inertial and gravitational effects of the orthesis. This allows complete closed-loop retrocontrol of the movements of the orthesis.

At the same time, the mathematical modelling of the behaviour of the muscles concerned is recorded in this software, so as to allow the closed-loop retrocontrol of the stimulation device.

This information thus constitutes a complete coordinated double retrocontrol of the activity under resistance load of each articulation. This technical retrocontrol is thus substituted for the absence of physiological retrocontrol, which is normally transmitted to the central nervous system (CNS) by the proprioceptive nervous system. In fact the technical retrocontrol closely mimics the deficient physiological retrocontrol.

The essential aim being to generate duly controlled movements, executed against preprogrammed fixed or changing loads, the programming of the stimulator 33 is envisaged in two ways, which may prove complementary, the second being able to serve to adjust the parameters of the first:

1. Analysis of the electromyograms of identical movements, executed in intentional mode by a healthy person, and then programming of the muscular sequence-based on these data, with a view to reproducing the movements.

2. Purely experimental programming of the movements by theoretical pre-establishment of the muscular sequence, and then testing and adjusting the parameters according to the reactions of the patient.

In all cases, provision is made for the operator to be able to intervene easily during stimulation in order to modify the muscular sequence, that is to say the start and end of activity of a channel in the given cycle, as well as the adjustment of the intensity of the contraction.

The training programs can be specifically established for a given patient, according to his morphology, his physiological capacities and reactions, his requirements and the objectives aimed at.

A specific training program for a given patient can be recorded in advance on a removable data medium 39 such as, for example, a diskette or a memory card. This data medium can be inserted in the control unit so that the management microcomputer 31 can control the neuromuscular stimulator 33 and the servomotors 20, 21, 22 with a view to implementing the said training program.

The execution according to a training program is controlled by a so-called "compliance" device which enters on the data medium 39 the value of any difference in execution of each of the initially programmed parameters. This compliance can then be interpreted by the operator by means of a re-reading of the data medium.

The specialised literature shows that if, during the execution of movements caused by neuromuscular electrostimulation, the patient can be encouraged to think of improving the activity thus achieved of the lower limbs, such a mental task may have a marked beneficial effect which facilitates the current activity.

Consequently there can be added to the training device a "biofeedback" system which can for example consist of a display, on a screen 40 placed in front of the exercising patient, of the level of the performance achieved, in terms of absolute value, and/or with respect to a fixed objective, and/or the progress accomplished.

The execution according to a programmed movement, and to a series of programmed movements (for example walking) is duly subjected to retrocontrol, executed by means of the information transmitted to the management microcomputer 31 of the central control unit by means of the position sensors 34, and the force and torque sensors 35 integrated in each orthetic articulation. This information is processed by the management microcomputer 31, duly programmed for this purpose, and subsequently serves to modulate the stimulation parameters which determine the duration and force of a contraction such as, for example, the duration of stimulation, the intensity of the current and the frequency of repetition of the impulses during stimulation.

As a result all the information supplied by the articular sensors (the output signal of the stimulated muscle), their processing within the microcomputer by means of a suitable program and the modulation of the stimulation which depends thereon (the input signal of the stimulated muscle) constitutes a closed-loop controlled retrocontrol system. Such a system defines a closed-loop controlled electrical muscle stimulation capable of generating duly controlled and repeatable movements, executed counter to preprogrammed fixed or changing resistance loads, unlike a conventional stimulation, open-loop controlled, where there is no retrocontrol of the muscular activity obtained.

The hybrid orthetic device described above, combining and coordinating the properties of a closed-loop retrocontrolled electrical muscular stimulation and a motorised functional mechanical orthesis, also closed-loop retrocontrolled, constitutes a robotic system allowing extreme versatility of application, since it can work equally well:

in training, in the case where the patient no longer has any strength and is not electrostimulated; in this case, only the motors at the articulations drive the programmed movements;

in compensation, when the patient—electrostimulated or not—does not have sufficient strength to execute the movements alone and must be able to be assisted, also with compensation for gravity; in this case, the motors at the articulations afford the necessary supplementary assistance;

in braking, the patient will generate—by stimulation and/or intentionally—a movement against which the device will be opposed partly or completely, by means of the servomotors 20, 21, 22, according to the resistance load programmed;

thus, according to the programming used:

if the load resistance completely opposes the movement, the training will be isometric;

if the load resistance constantly adapts in order to maintain a constant articular angular speed of movement, the training will be isokinetic;

if the articular angular speed adapts constantly in order to maintain a constant load resistance, the training will be isotonic;

each articulation can be trained individually against a programmed resistance load which is peculiar to it. Thus, for example, it is possible, with the leg in extension, to train, at the ankle articulation, the plantar flexion (that is to say the extension of the foot) counter to a resistance load. Such a training makes it possible to mimic an elevation on the tip of the feet against a progressive resistance load. The latter can be increased gradually up to, for example, a maximum of 100 kg per leg. It is thus possible to strengthen the articulation and the musculi gemelli situated in the posterior lodge of the leg and which contribute to an essential extent to the impetus force pulse in the process of walking;

the body segments which constitute the lower limb and their articulations can be trained in a coordinated manner, in accordance with the kinematic chain which they constitute, in order to produce specific movements:

for example, in order to produce simultaneous extension movements of the two lower limbs, followed by flexion movements counter to a resistance load, so as to mimic the movements of passing from a crouching position to an extension position, corresponding to a vertical position of the body, supported against gravity, and then return in a controlled manner to the crouching position;

for example, in order to produce alternating movements of pedalling the two lower limbs against the braking resulting from a programmed resistance load;

for example, in order to produce, by mimicry, the basic training of the alternating movements of the two limbs during walking (stepping) counter to the corresponding resistances at the articulations.

Figure 5B:
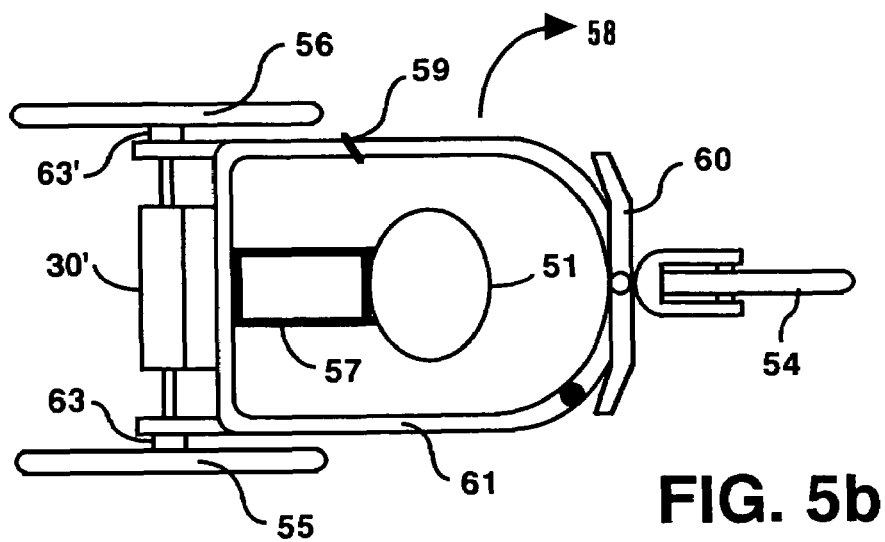
Figure 6:
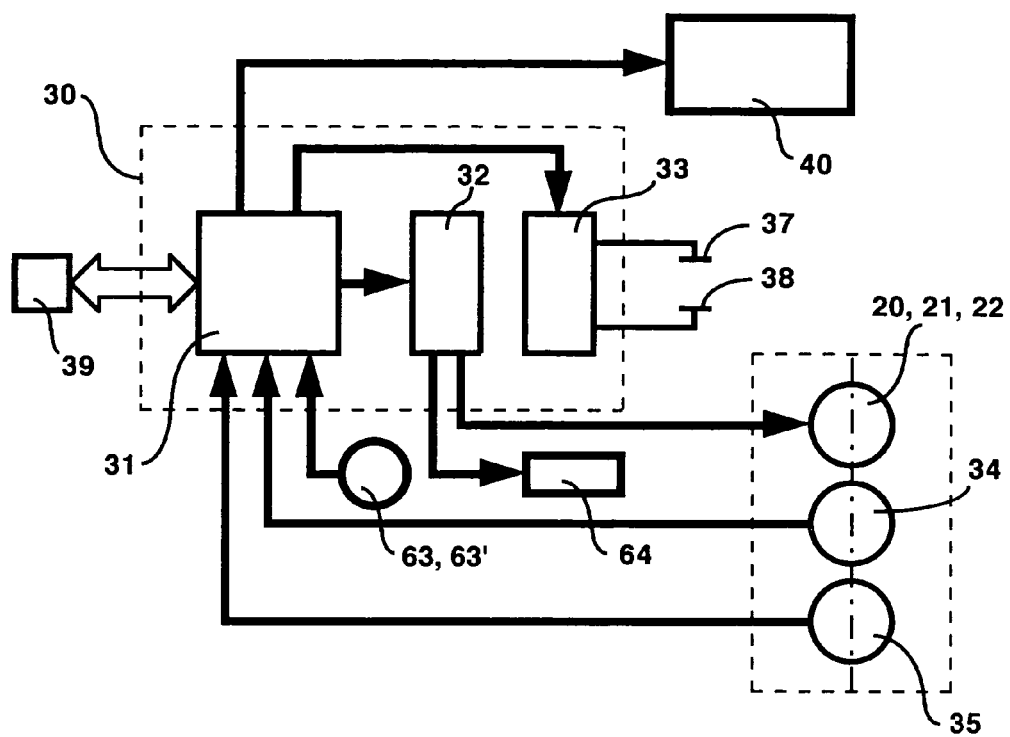
FIG. 6 shows a block diagram of the articular motorisation system of the device of FIG. 5 and its retrocontrol.

According to a second embodiment depicted in FIGS. 5a, 5b and 6, the device comprises a hybrid orthesis for training the lower limbs similar to that in FIG. 1, but arranged for a use in the vertical position, with a view to the specific training of the dynamic process of walking, respecting the inherent movement, when the patient has recovered suitable "fitness" (degrees of musculation and articular mobility) of the lower limbs, in order to train the patient specifically for walking by means of a close mimicry of the dynamic process of intentional walking.

To this end, all the elements of the device according to the first embodiment, with the exception of the horizontal frame 10 intended to support the back and the pelvis of the patient in the position lying on the back, can be reused, the two identical ortheses intended for the two legs being in this case fixed on each side of a mechanical pelvic belt 51, adjustable so that the orthetic articulations of the hip coincide from a functional point of view with the corresponding physiological articulations of the patient. The pelvic belt, constituting in some way an exopelvis, is provided with a kind of shorts 52 which constitute a harness intended to support the trunk of the patient.

The assembly consisting of the pelvic belt and the harness shorts also contributes to providing the vertical stability of the trunk. According to circumstances, this assembly can also be supplemented by two lateral uprights, joined by a thoracic belt in order to improve the vertical stability of the trunk still further.

The pelvic belt 51 is fixed by a mechanical device articulated on a movable frame 53, a light structure provided with three wheels 54, 55, 56 in order to provide its movement on the floor in the direction of the walking. The mechanical device connecting the pelvic belt with the frame is designed so that it allows only a vertical movement of the pelvic belt, to enable it to follow the slight vertical reciprocating movement due to the parabolic path which develops during walking. In addition, this device must be sufficiently rigid to provide stability of the pelvic belt on the horizontal plane and its following of the path imposed by the frame during a change of direction imposed by the moving patient. By way of example, such a mechanical connection device can be produced by means of an articulated parallelogram 57 placed in the longitudinal vertical plane, where one of the vertical elements is fixed to the frame and the other vertical element on the opposite side is fixed to the pelvic belt by means of a quick-locking removable fixing. The parallelogram can be provided with a motorisation device, such as for example a servomotor acting in the vertical plane and slaved to force and torque as well as position sensors. Such a device is thus capable of supporting in whole or in part the weight of the body during its movement. The chassis can also open on one of its sides 58, the quick-locking uprights 59 of which can pivot forwards in order to leave clear access to the inside of the frame.

In fact, provision is made for equipping the patient in advance with his orthesis, and then introducing it inside the frame and fixing the pelvic belt to its connecting device with the said chassis.

The front wheel 54 can be steered, controlled by handlebars 60 actuated manually by the patient, in order to effect changes of direction and, in particular, provide an outward and return journey on the training track. It is also possible to use a device of the idle wheel type. In this case, the changes in direction are imposed by the change in the direction of the walking of the patient, a change in direction caused by the stimulation device. To this end, contrary to what is illustrated in FIG. 5b, the optimum position of the patient is in the axis of the rear wheels. According to this variant, the handlebars can of course be kept so as to allow manual corrections to the steering.

The frame is provided on its periphery with a balustrade, or support ramp 61 within reach of the hand of the patient. This ramp, and the pelvic belt and the steering handlebars, are adjustable for height in order to be able to be adapted to the morphology of the patient.

The central control unit 30' is also fixed to the said frame, as is a control 62 placed within reach of the hand of the patient, in order to start up, control the speed, and then stop the training during running.

Given that, when there is a change of direction imposed by the patient, the wheel external to the turn follows a longer path than the inner wheel, the same will apply to the greater path to be travelled by the strides external to the turn than the strides internal to the turn of the patient. Consequently, in order to avoid an excessively high differential physiological stress on the lower limbs, the two wheels concerned are provided with digital coding sensors 63, 63', the information from which, processed by the central control unit, acts accordingly on the stimulation closed-loop control, in order to suitably modify the muscular stimulation applied to the two legs.

Although such a process is somewhat simplistic and does not fulfil all the physiological conditions of an intentional change in direction, it nevertheless proves sufficient in the case of the training described here.

The movable frame can be provided with a brake 64, acting for example on the front wheel. This brake is duly slaved to the speed of movement of the patient and by means of the digital coders 63, 63' of the rear wheels in order to perfectly synchronise the speed of movement of the frame with the inherent speed of movement of the patient due to his walking activity.

The movable frame can also have its own drive device, consisting for example of one or more motors or servomotors 65, 66 slaved to the central control unit 31 and acting on one or more of the wheels 54, 55, 56, in order to perfectly synchronise the speed of movement of the movable chassis with the inherent speed of movement of the patient due to his walking activity. Such an arrangement is in particular especially useful in the case where the movable chassis is burdened by the presence of batteries for its electrical supply.

The device described above has the fundamental advantage that it makes it possible to achieve training for walking absolutely in accordance with his dynamic intentional physiological process, which it makes it possible to mimic perfectly.

Thus muscular stimulation according to the known process of walking, achieved in a perfectly retrocontrolled manner by closed-loop control (see diagram in FIG. 6 similar to that in FIG. 4), can make it possible to give the perfectly apportioned impetus impulse, essential for causing propulsion. Accordingly, the weight of the body undergoes acceleration and acquires a certain speed of movement. The result is the creation of a kinetic energy and a quantity of movement. The device proposed, which allows effective movement, following walking, consequently allows management of the kinetic energy thus created and, in particular, conservation of the quantity of movement, almost identical to what is achieved during equivalent intentional walking. As the system allows partial or complete take over of the weight of the body by the lower limbs during walking, the work carried out, the speed of movement achieved and, finally, the necessary energy consumed are practically identical to those of an equivalent intentional movement.

Under these circumstances, the proprioceptive impulses delivered to the central nervous system are very close to those supplied by intentional training. Consequently they may have optimum stimulation action on the capacity for substitution by plasticity of the central nervous system, with a view to testing and then training possible restoration of satisfactory intentional walking from a functional point of view, when the spinal cord is only partially affected. For the same reasons, the reteaching of the walking motor scheme is optimum.

According to a variant of the second embodiment which has just been described, the articulations 6, 7 and 8 have no motors or brakes. However, naturally, the angular sensors and the force sensors remain necessary.

Moreover, whatever the embodiment, the motors may not be embarked on the ortheses but be mounted on any other support, for example the support 10 in FIG. 1 or on the movable support device of FIGS. 5*a* and 5*b*, and mechanically connected to their corresponding gearboxes by means of a control at a distance, for example with transmission by chains and gears.

Naturally all the devices described above can also be used in the field of sports training.

What is claimed is:

1. A device for re-educating and/or training the lower limbs of a person, in particular a person having an impairment of the central nervous system (paraplegia, hemiplegia), comprising a mechanical orthetic device arranged to constitute an interface with at least one of the lower limbs of the patient and a neuromuscular stimulation device comprising at least one pair of electrodes intended to act on the relevant muscle or muscle group of the said limb of the patient, the said orthetic device comprising at least one articulation provided with an actuating motor of the orthesis and with an angular sensor and at least one force sensor, the said sensors being coupled to a control device controlling the stimulation device, with closed-loop continuously controlled in real time retrocontrol means of said stimulation device, thereby generating a neuromuscular stimulation providing an active motion of said limbs of the patient, in a manner which is coordinated with a closed-loop continuous control system controlling said actuating motor of the orthesis in real time by means of the said angular sensor and force sensor, whereby said actuating motor of the orthesis provides counter pre-programmed resistance loads and compensates the gravity and inertial effects of the orthesis.

2. A device according to claim 1, wherein said control system of the motor comprises a control software of the a priori type.

3. A device according to claim 1, wherein said retrocontrol means of said stimulation device comprise a control software of the a priori type.

4. A device according to claim 1, wherein said control software incorporate a mathematical modelling of the characteristics and movements of the orthetic device and a mathematical modelling of the behaviour of the muscles of the patient.

5. A device according to claim 1, wherein the orthetic device comprises at least one orthesis comprising at least three segments intended to constitute a mechanical interface with respectively the thigh, the leg and the foot of the patient, the first and second segments comprising means for their respective connections to the thigh and to the leg of the patient and the third segment being disposed so as to constitute a plantar support and comprising means for its fixing to the foot of the patient, the first segment being connected firstly at one of its ends by a first motorised articulation to an element arranged so as to cooperate with the body of the patient at his hips and on the other hand at its other end by a second motorised articulation to one of the ends of the second segment, the other end of the said second segment being connected by a third motorised articulation to the third segment.

6. A device according to claim 1, comprising two said ortheses, each of which is arranged so as to constitute an interface with one of the lower limbs of the patient.

7. A device according to claim 5, wherein said first and second segments consist of elements with adjustable lengths, so as to be able to adapt their length to the morphology of the patient.

8. A device according to claim 5, wherein each of the articulations of the orthetic device is secured to an electric servomotor coupled to a gearbox.

9. A device according to claim 8, wherein the shaft of said servomotor is parallel to an adjacent orthesis segment and in that it drives a perpendicular shaft of the articulation by means of a pair of bevel gears.

10. A device according to claim 5, wherein each of the articulations of the orthetic device is secured to an electric servomotor coupled to a gearbox, each servomotor comprising a shaft, and wherein the servomotor is fixed to one of the orthesis segments attached to the articulation and rotationally drives a worm, on which a nut is mounted which in its turn drives the movement of a crank, fixed to the second orthesis segment, and whose rotation axis corresponds to a rotation axis of the articulation.

11. A device according to claim 10, wherein the shaft of each of the servomotors is perpendicular to the orthesis segment adjacent to the servomotor.

12. A device according to claim 10, wherein each of the servomotors incorporates a digital position coder and in that force and torque sensors are integrated in each articulation.

13. A device according to claim 10, wherein the servomotors are slaved to the control device and in that the latter comprises separate control means for each of the said motors.

14. A device according to claim 1, wherein the orthetic device is fixed to a horizontal frame arranged so as to support the back and pelvis of the patient for driving his lower limbs in the horizontal position.

15. A device according to claim 1, wherein the orthetic device is fixed to a mechanical pelvic belt arranged so as to be placed around the hips of the patient for driving the lower limbs of the patient in the vertical position, the said pelvic belt comprising members for fixing said pelvic belt to a movable support device so as to enable the patient to move.

16. A device according to claim 15, wherein the pelvic belt is fixed to the movable support by an articulated mechanism.

17. A device according to claim 16, wherein the said articulated mechanism is provided with a motorisation device acting in the vertical plane and slaved to force, torque and position sensors, so as to wholly or partly support the weight of the body of the patient during his movement.

18. A device according to claim 15, wherein said support device is mounted on wheels.

19. A device according to claim 15, wherein said device comprises its own drive device slaved to the control device.

20. A device according to claim 1, wherein the control system comprises a microcomputer.

21. A device according to claim 20, wherein the control system comprises reading means intended to cooperate with removable data media so as to enable individualised training programs to be produced.

22. A device according to claim 1, comprising display means intended in particular to inform the patient in real time of his performance level.

* * * * *